United States Patent [19]

Chong

[11] Patent Number: 4,981,132
[45] Date of Patent: Jan. 1, 1991

[54] ORTHOSIS FOR THE TREATMENT OF TIBIAL TORSION IN CHILDREN

[76] Inventor: Andrew Chong, 501 E. Prairie, Wheaton, Ill. 60187

[21] Appl. No.: 516,316

[22] Filed: Apr. 30, 1990

[51] Int. Cl.⁵ ............................................. A61F 5/00
[52] U.S. Cl. ................................. 128/80 R; 128/80 A
[58] Field of Search .................. 128/882, 80 R, 80 A, 128/80 B, 80 C, 80 J, 80 G

[56] References Cited

U.S. PATENT DOCUMENTS

| | | | |
|---|---|---|---|
| 3,958,567 | 5/1976 | Callender, Jr. | 128/80 R |
| 4,295,466 | 10/1981 | Prout | 128/80 R |
| 4,407,276 | 10/1983 | Bledsoe | 128/80 C |
| 4,554,912 | 11/1985 | Haberman | 128/80 E |
| 4,632,096 | 12/1986 | Harris | 128/80 C |
| 4,922,895 | 5/1990 | Chong | 128/80 J |

Primary Examiner—Robert A. Hafer
Assistant Examiner—Kerry Owens
Attorney, Agent, or Firm—Allegretti & Witcoff, Ltd.

[57] ABSTRACT

A molded plastic orthosis for treating tibial torsion in children without twisting the femur or hip, and which is adjustable to accommodate the growth of the child's leg. The orthosis is made of two braces, a first brace which embraces the tibia and the foot, and a second brace embracing the upper end of the tibia and the femur with the knee in flexed position. The tibial portion of the second brace overlaps the tibia portion of the first brace, and the overlapping portions are surfaced with Velcro fasteners for adjustably locking the two braces against rotation.

7 Claims, 2 Drawing Sheets

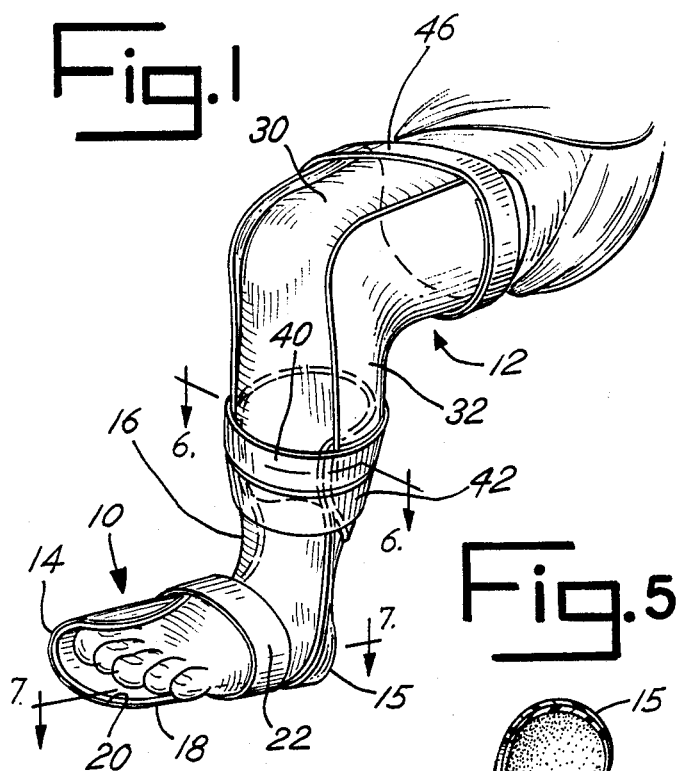
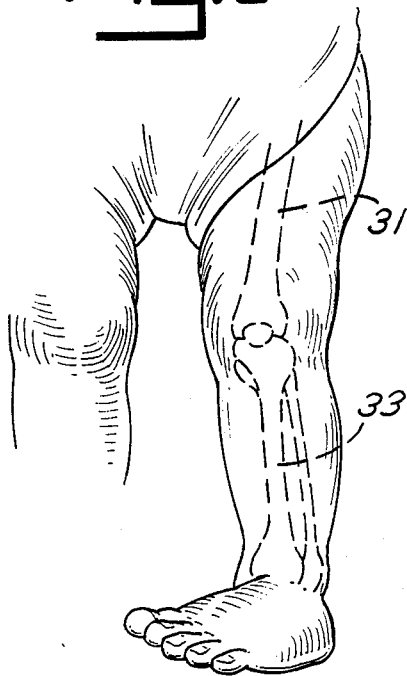
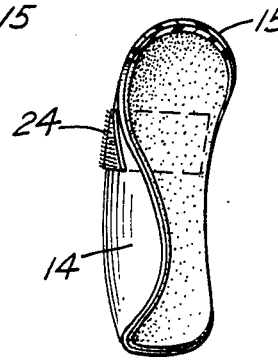
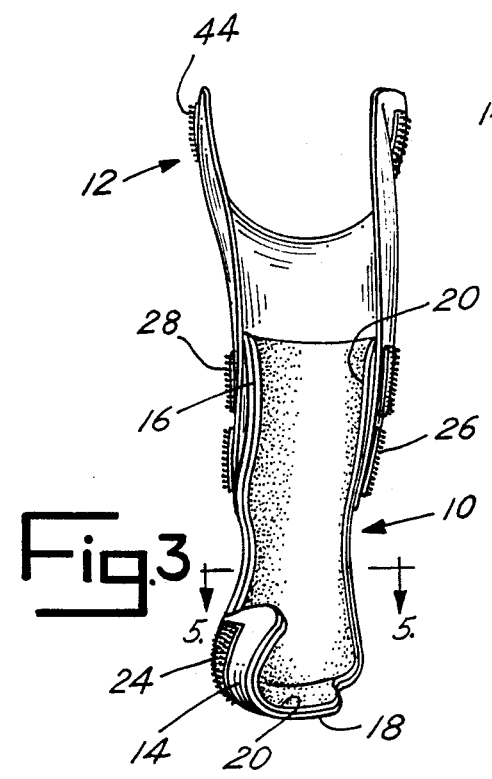
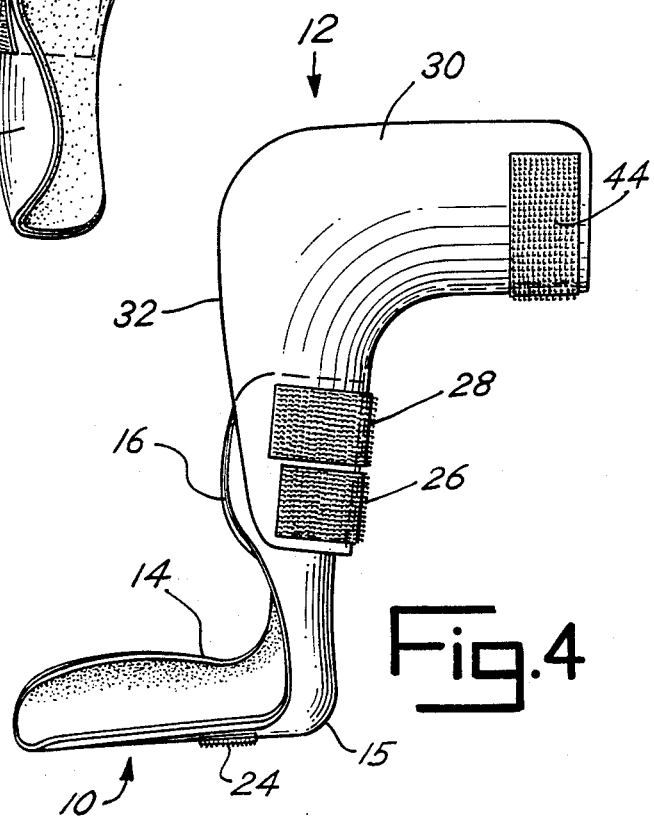

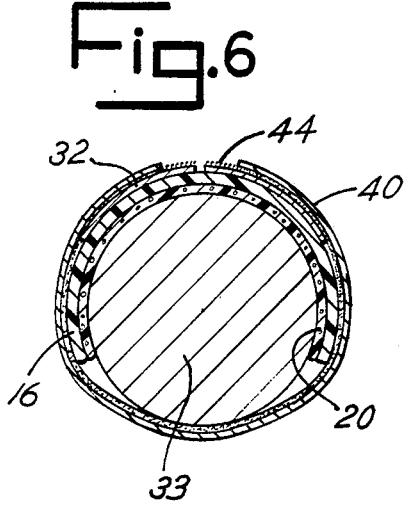
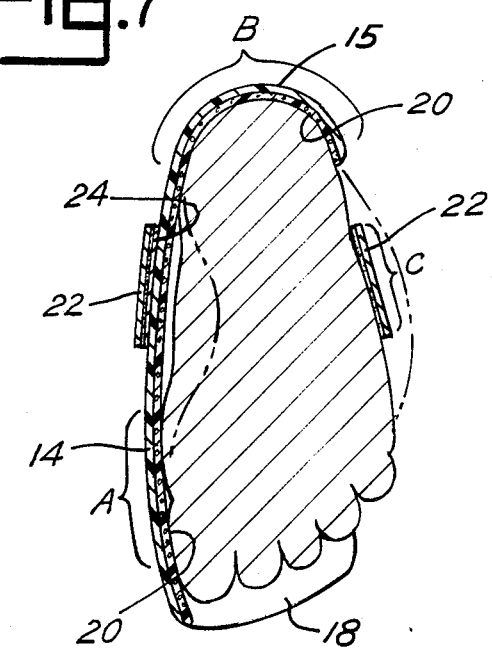
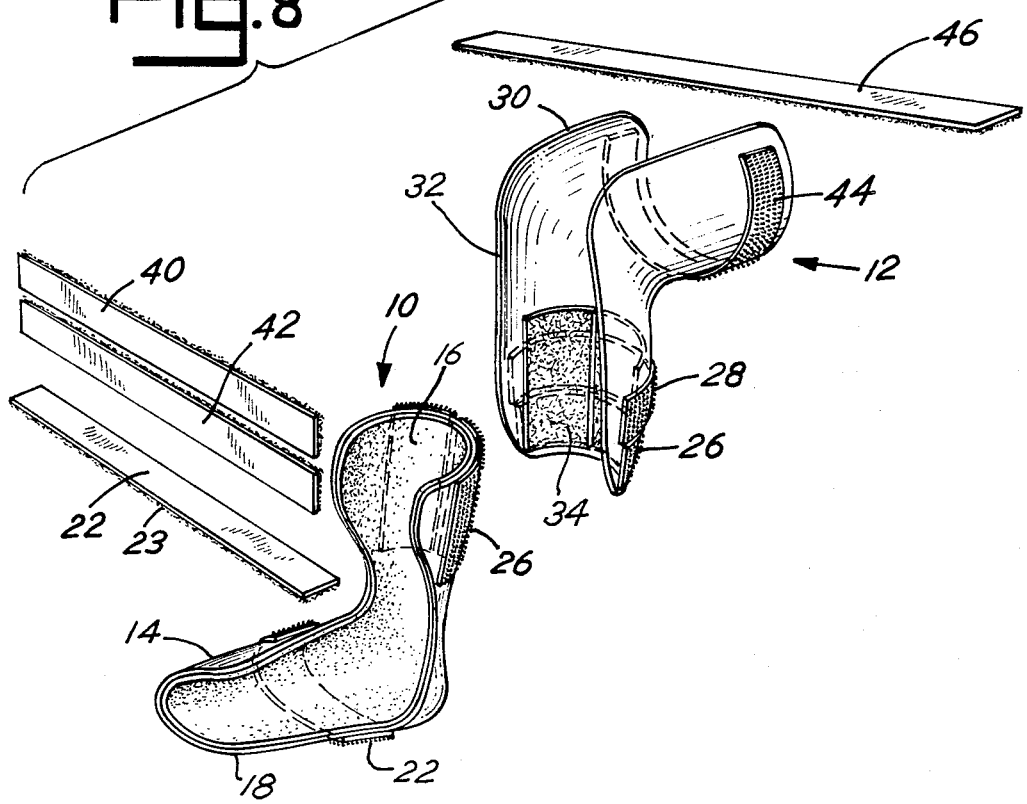

ORTHOSIS FOR THE TREATMENT OF TIBIAL TORSION IN CHILDREN

BACKGROUND OF THE INVENTION

Tibial torsion is and orthopedic condition in children where the tibia (leg bone) is twisted about its longitudinal axis. It may be twisted inwards (the condition being called internal tibial torsion) or outwards (the condition being called external tibial torsion). Internal tibial torsion is by far more common than external tibial torsion. Internal tibial torsion may occur by itself, but is commonly associated with metatarsus adductus (turning in of the forefoot) or congenital clubfoot (turning in of the forefoot and turning inwards and downwards of the heel).

The treatment of tibial torsion has traditionally been by use of the Denis-Browne bar and shoes, or long leg casts. The Denis-Browne Bar consists of a rigid bar connecting at each end to the sole of the child's shoes and holding the child's legs apart. The legs are rotated externally (outwards) or internally (inwards) to effect the necessary correction. The Denis-Browne bar has been in common use for decades, but has been notorious for poor patient acceptance because of the restriction and discomfort it inflicts on the child. More reecently, an articulated bar with hinges along its length was developed (Counter Rotation System by Langer Biomechanics Group, Deer Park, N. Y.) to allow less restriction on the child, and hopefully better acceptance. The problems, however, remain and are two-fold:

1. The corrective force is not directed to the tibia where the problem is. Because the knees are in the extended (straight) position as the shoes are rotated on the bar, most of the rotational force is spent on the femur and the hip rather than the tibia.

2. Both legs have to be splinted, whether the tibial torsion is unilateral or bilateral.

Serial castings is another commonly used method of treatment of tibial torsion, especially when there is associated foot deformity (as in metatarsus adductus or clubfoot). The cast is applied with the knee in the flexed position and can be effective. However, it means repeatedly changing the casts biweekly for a period of months. It is time-consuming, inconvenient, uncomfortable and expensive.

Phillips et al. (U.S. Pat. No. 4,543,948) describes an apparatus and method for applying rotational pressure to parts of the body, including the tibia. Following the teachings of Phillips, the following problems were encountered:

1. It is virtually impossible to rotate the tibia without also rotating the femur and hip, as long as the knee is in the extended position. The drawings in the Phillips patent show the knee in extended position. While phillips stressed that "the important thing is that there be little or no substantial relative rotational movement betwween the cast and the part of the body within the cast" (column 6, line 67), he did not teach how this was to be achieved. Keeping the knee extended certainly makes this impossible to achieve, since the axis of the torque of the tibia and the femur are one and the same. Since this patent was published in 1985, no significant commercialization of this device or method of treating tibial torsion has been forthcoming, as far as can be determined.

2. Following Phillip's teaching to allow for the growth of the child, multiple sizes of the cast or brace would be necessary for any single child, since the course of treatment usually takes 6 to 12 months.

More recently, the Bremer Medical Companies, Jacksonville, Fla., have developed the "Tibial Torsion Transformer" which corrects the tibial torsion by torquing the tibia with the knee in the flexed position. It also has adjustment to allow for growth in tibial length. However, the device is made of metal, and adjustment involves use of hardware (nut and bolt), making its use quite cumbersome. Also, the device does not treat any associated foot disorders. This means that a separate device will have to be used in addition to the Bremer device to treat metatarsus adductus, for example.

There is a real need for a device that satisfies the following criteria:

1. Treats the tibial torsion directly without twisting the femur or hip at the same time. The device must therefore maintain the knee in the flexed position.

2. Treats only the side involved, allowing the uninvolved leg to be completely free from splinting.

3. Adjustable to allow for the growth of the child obviating the need for multiple sizes during treatment.

4. Fast and easy application and adjustment, without use of cumbersome hardware. (Most doctors' offices do not carry screwdrivers and pliers.)

5. Treats any associated forefoot adductus, as well as tibial torsion.

SUMMARY OF THE INVENTION

The present invention consists of two components.

1. The Lower Component

The Wheaton Brace (Ref. U.S. patent application Ser. No. 677,372 filed Dec. 1984, now U.S. Pat. No. 4,922,895), an ankle-foot orthosis made of a thermoplastic material, holds the tibia and foot as one unit, extending from the upper part of the tibia to the distal part of the foot, including the toes. This serves a dual purpose. (1) When combined with the upper component, it serves as a lever for rotating the tibia to correct the tibial torsion; and (2) by itself, it corrects any associated foot deformity by using the three-point fixation principle disclosed in patent aplication Ser. No. 677,372. For the treatment of clubfoot, the ankle has to be set at 90 degrees (dorsiflexed position).

2. The Upper Component

A knee orthosis encloses and extends from the posterior part of the upper femur to the posterior part of the lower tibia, and, by adjustable straps, holds the knee in 90 degree flexion. It is essential that the knee be in the 90 degree flexed position. As long as the knee is in the extended position, both the longitudinal rotational axes of the tibia and femur are one and the same, so that any rotational force applied on the tibia will rotate the femur and hip as well. But with the knee flexed to 90 degrees, the longitudinal axis of the tibia is now perpendicular to the longitudinal axis of the femur, and any rotational force applied upon the tibia is not translated to the femur or the hip.

The upper and lower components overlap at the tibia, and preferably are attached to each other by use of hook and loop fasteners (Velcro). By telescoping the lower and upper components, one can adjust for growth in leg length. Bt rotating the lower component with respect to the upper component and locking it in the oriented position, rotational force can be applied directly on the tibia.

THE DRAWINGS

The objects of this invention will be explained more fully in connection with the illustrative embodiment shown in the drawings in which FIG. 1 is a perspective view of a child's leg fitted with the two-component orthosis of the invention.

FIG. 2 illustrates a child's leg in extended position with the tibia and femur shown in dotted lines.

FIG. 3 is a front elevational view, partly in section, showing both components in assembled condition.

FIG. 4 is a side elevational view of the two-component orthosis of FIG. 3.

FIG. 5 is a sectional view taken along the line 5—5 of FIG. 3.

FIG. 6 is a sectional view taken along the line 6—6 of FIG. 1.

FIG. 7 is a sectional view taken along the line 7—7 of FIG. 1, the deformation of the child's foot shown in phantom lines.

FIG. 8 is an exploded view of the upper and lower components, together with the cooperating straps of the orthosis.

DETAILED DESCRIPTION

The ankle-foot orthosis or the lower component of the two-component assembly is designated by the numeral 10 while the unitary knee orthosis or upper component is designated generally by the numeral 12. The lower component 10 has a foot embracing portion 14 which is curved to enclose the medial side of the child's foot. Component 10 also includes a heel embracing portion 15 which merges with the foot portion 18 and the tibia embracing portion 16 of the ankle-foot orthosis. The lower component is molded from a thermoplastic resin such as polypropylene and the inner surface thereof is lined with a cushioning material 20 such as plastic foam against which the child's leg is secured by means of straps. A strip of a hook and loop fastener 24, preferably Velcro, is adhered to the outer surface of the sole member 18 and the foot embracing portion 14. This strip 24 is disposed just forward of the heel and cooperates with a strap 22 which also has a loop and hook fastener surface 23 (FIG. 8) which cooperates with the similar Velcro surface 24. This strap is used to secure the foot in the orthosis and to apply pressure against the deformation in the area C as indicated in FIG. 7, where the child is afflicted with metatarsus adductus, as well as tibial torsion. The medial side of the foot bears against the fixed area A and the heel bears against the fixed area B of the lower component. The strap 22 is tightened gradually over time to reduce the distortion by applyig a force which is resisted by the fixed areas A and B of the orthosis.

The outer surface toward the top of the tibia embracing portion 16 of the orthosis 10 is covered with a Velcro pad 26 encirling this curved rear surface. This hook and loop fastener cooperates with a similar pad 34 on the interior surface of the upper component as explained below.

The unitary knee orthosis or upper component 12 is molded from the thermoplastic resin and consists of a vertical portion 32 which embraces the rear portion off the tibia 33 and a horizontal portion 30 which embraces the underside of the femur 31. This unitary knee orthosis encloses the back of the knee and extends from the femur to the tibia, holding the knee at 90 degrees flexion. The inner surface of the portion 32 of the upper component is covered with a pad of Velcro hook and loop fastener 34 as best shown in FIG. 8. The pad 34, securely adhered to portion 32, cooperates with the fastener pad 26 on the backside of the lower component to lock the two components against rotation when the lower component is inserted between the two sides of the portion 32 of the upper component. The lower component is positioned with respect to the lower component by turning it to the desired orientation and the desired height before inserting it within the upper component and engaging the fastener pads 26 and 34. The Velcro pads lock the parts securely together so that once engaged, the parts will not rotate with respect to each other. Neither will the parts move vertically with respect to each other.

The plastic material from which the components are molded permit some flexing. The sides of the portion 32 may be readily separated manually, and the sides of the portion 16 may be pushed together to facilitate engagement of the overlapping parts.

Velcro strips 28, 26 are secure to the outer surface of the lower vertical portion 32 of the knee orthosis 12. These strips cooperate with strips 42, 40 which encircle the lower end of the vertical portion 32 of the upper component as well as the upper part of the vertical tibia embracing portion 16 and the leg of the child as best shown in FIG. 1. Another Velcro strip 44 is adhered to the outer surface of the portion 30 and Velcro strap 46 cooperates with the strip 44 to secure the unitary knee orthosis 12 to the leg of the child as shown in FIG. 1. When the orthosis and the cooperating straps are in operative position as shown in FIG. 1, the knee orthosis holds the knee in 90 degree flexion thus isolating any rotational force on the tibia from the femur. The strap 22 holds the foot against the curved surface 14 of the ankle foot orthosis to correct the tibial torsion in proportion to the degree of the rotation of the lower component 10 with respect to the upper component 12.

Since the two components overlap, adjustment can be made for growth in tibia length of the child. The extent of the overlap is sufficiently large so that the two-component device can be lengthened without loss of function. By rotating the ankle foot orthosis relative to the knee orthosis, rotational force is applied selectively on the tibia. As indicated, th Velcro fasteners allow for easy adjustment and readjustment for both leg length growth and desired rotational force on the tibia. For internal tibial torsion, the suggested position is between 30 degrees and 40 degrees of external rotation.

Other devices than the ankle-foot orthosis shown in the drawing can be used as the lower component. This orthosis is preferred, however, where the child is suffering from metatarsus adductus in addition to tibial torsion. The ankle-foot orthosis may be modified to lock the foot to the sole 18 in ways other than that shown, particularly if the case does not require simultaneous correction of metatarsus adductus. The lower component must include The overlapping Velcro interlock 26, 34 in order to produce the desired rotational force. The foot portion of the member 10 must be capable of retaining the foot in the rotated position. If the foot and the tibia is permittd to turn with respect to the lower component, then of course, the device will not be effective for correcting tibial torsion. The device of the invention applies direct rotational force on the tibia without rotating the femur or the hip, unlike the Denis-Browne bar. There is no cumbersome hardware to deal with. The brace can be lengthened with the growth of the child and is effective during the entire time of treatment. Unlike the bar, the device of the invention treats only the affected leg. The device can be made in different sizes to fit children from age 1 to age 4. The device of the invention is comfortable for the child and is esily removed for purposes of inspection of the skin.

What is claimed is:

1. An orthosis for the treatment of tibial torsion in children comprising:
    a unitary ankle-foot orthosis having a tibia-embracing section and a foot embracing section,
    a unitary knee orthosis having a first portion for embracing the posterior of the tibia and a second portion extending approximately normal to said first portion, for embracing the posterior of the femur, the first portion of said knee orthosis overlapping the tibia-embracing section of said ankle-foot orthosis,
    means on said ankle-foot orthosis and on said knee orthosis for securing said orthoses to the foot, the tibia and the femur, and
    cooperating fastener means secured to the outer surface of the overlapping part of said tibia-embracing section and to the inner surface of the overlapping part of said first portion of said knee orthosis for locking said parts against rotation.

2. The orthosis of claim 1 in which said unitary ankle-foot orthosis and said unitary knee orthosis are molded from flexible thermoplastic resin.

3. The orthosis of claim 2 in which said cooperating surfaces of said orthoses have hook and loop fasteners.

4. The orthosis of claim 2 in which said overlapping part of said first portion of said knee orthosis snaps over the overlapping part of said tibia-embracing section of said ankl-foot orthosis.

5. The orthosis of claim 1 in which said securing means comprises adjustable straps encircling the foot, the tibia and the femur.

6. The orthosis of claim 5 wherein said tibia-encircling adjustable strap encloses both of said overlapping portions.

7. The orthosis of claim 2 which includs a cushion lining in said ankle-foot orthosis.

* * * * *